US00PP25950P3

(12) United States Plant Patent
Meilland

(10) Patent No.: US PP25,950 P3
(45) Date of Patent: Sep. 29, 2015

(54) FLORIBUNDA ROSE PLANT NAMED 'MEIGREMLIS'

(50) Latin Name: *Rosa hybrida*
Varietal Denomination: Meigremlis

(71) Applicant: CP DELAWARE, INC., Wilmington, DE (US)

(72) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 99 days.

(21) Appl. No.: 13/998,747

(22) Filed: Dec. 3, 2013

(65) Prior Publication Data

US 2015/0156933 P1 Jun. 4, 2015

(51) Int. Cl.
*A01H 5/02* (2006.01)

(52) U.S. Cl.
USPC ..... Plt./151

(58) Field of Classification Search
USPC ..... Plt./101, 141, 151
See application file for complete search history.

*Primary Examiner* — Susan McCormick Ewoldt
(74) *Attorney, Agent, or Firm* — Buchanan, Ingersoll & Rooney PC

(57) ABSTRACT

A new and distinct Floribunda rose plant is provided that commonly commences blooming early in the season and forms abundantly and substantially continuously attractive red semi-double blossoms. The growth habit is low, compact, and bushy. Strong vegetation is formed. The plant commonly displays a well-ordered overall appearance until late in the season. The vegetation is dense and bears a glossy aspect on the upper surface. No particular disease problem has been observed. The plant is particularly well suited for providing attractive ornamentation in parks and gardens.

1 Drawing Sheet

Figures 1, 2, 3, 4, 5, 6, 7, 8, 9, 10, 11, 12, 13, 14, 15, 16, 17:
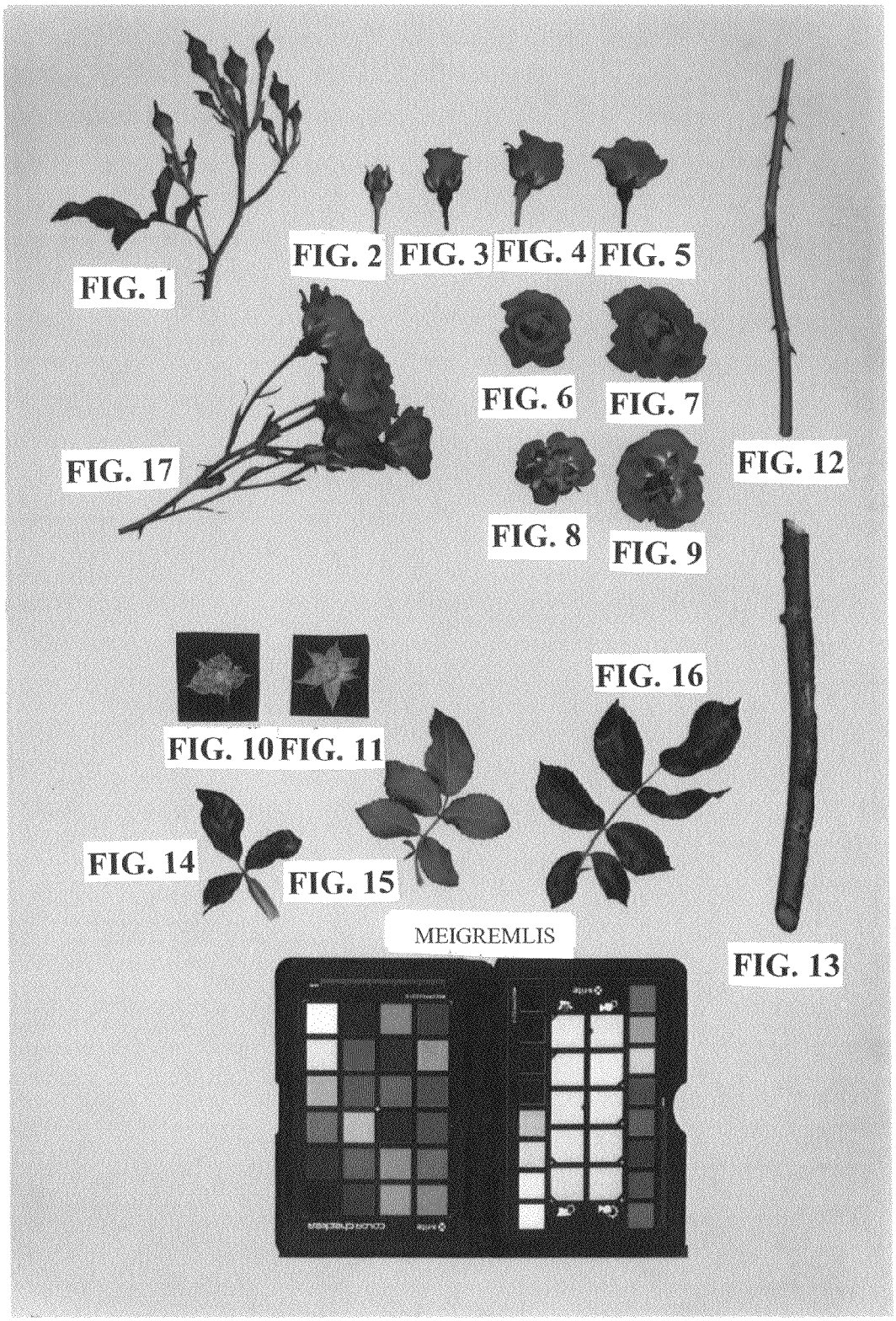

Botanical/commercial classification: *Rosa hybrida*/Floribunda Rose Plant.

Varietal denomination: cv. Meigremlis.

SUMMARY OF THE INVENTION

The new variety of *Rosa hybrida* Floribunda rose plant was created by artificial pollination wherein two parents were crossed which previously had been studied in the hope that they would contribute the desired characteristics. The female parent (i.e., the seed parent) was 'The Fairy' variety (non-patented). The male parent (i.e., the pollen parent) was the 'Kormax' variety (non-patented).

The parentage of the new variety can be summarized as follows:

'The Fairy'×'Kormax'.

The seeds resulting from the above pollination were sown and small plants were obtained which were physically and biologically different from each other. Selective study resulted in the identification of a single plant of the new variety.

It was found that the new Floribunda rose plant of the present invention:

(a) displays a low and compact bushy growth habit with strong vegetation with the plant commonly displaying a well-ordered overall appearance until late in the season,
(b) forms in abundance on a substantially continuous basis attractive red semi-double blossoms,
(c) exhibits rather dense dark green foliage with a glossy aspect on the upper surface, and
(d) is particularly well suited for providing attractive ornamentation in parks and gardens.

The blooming tends to commence early in the season, during observations to date.

The new variety well meets the needs of the horticultural industry and can be grown to advantage in parks and gardens where attractive ornamentation is to be provided.

The new variety can be readily distinguished from its ancestors. For instance, 'The Fairy' parental variety forms dissimilar light pink blossoms. The 'Kormax' parental variety forms dissimilar red blossoms commonly having only six petals per blossom.

This new variety also can be readily distinguished from the 'Meigalpio' (U.S. Plant Pat. No. 17,877) and 'Noatraum' (U.S. Plant Pat. No. 10,084) rose varieties. More specifically, the foliage of the 'Meigalpio' variety is less glossy on the upper surface, and the 'Noatraum' variety commonly displays a taller growth habit. The 'Noatraum' variety is also known as 'Naofeuer' in Europe.

The new variety has been found to undergo asexual propagation in France by a number of routes, including budding, grafting, and the use of cuttings. Asexual propagation by the above-mentioned techniques at Le Cannet des Maures, Var, France, has shown that the characteristics of the new variety are stable and are strictly transmissible by such asexual propagation from one generation to another. Accordingly, the new variety undergoes asexual propagation in a true-to-type manner.

The new variety has been named 'Meigremlis'.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately two years of age and were observed during April while growing outdoors at Le Gannet des Maures, Var, France. Comparative standard color information is provided at the bottom of the photograph.

FIG. 1—illustrates a specimen of a young shoot with unopened floral buds;

FIG. 2—illustrates a specimen of a floral bud at the opening of the sepals;

FIG. 3—illustrates a specimen of a floral bud wherein the sepals are more fully open;

FIG. 4—illustrates a specimen of a floral bud at the opening of the petals;

FIG. 5—illustrates a specimen of a flower in the course of opening;

FIG. 6—illustrates a specimen of an open flower—plan view—obverse;

FIG. 7—illustrates a specimen of a fully open flower—plan view—obverse;

FIG. 8—illustrates a specimen of an open flower—plan view—reverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates a specimen of a leaf with three leaflets—plan view—upper surface;

FIG. 15—illustrates a specimen of a leaf with five leaflets—plan view—under surface;

FIG. 16—illustrates a specimen of a leaf with seven leaflets—plan view—upper surface; and FIG. 17—illustrates a cluster of open flowers.

DETAILED BOTANICAL DESCRIPTION

The chart used in the identification of the colors is that of The Royal Horticultural Society (R.H.S. Colour Chart). The description is based on the observation of two-year-old plants during April while growing outdoors on their own roots at Le Cannet des Maures, Var, France.

Class: Floribunda.

Plant:

*Growth habit*.—Bushy.

*Height*.—Commonly approximately 40 cm on average.

*Width*.—Commonly approximately 40 cm on average.

Branches:

*Color*.—Young stems: near Yellow Green Group 146D. Adult wood: near Yellow Green Group 146D.

*Thorns*.—On young stems: Configuration: with an oval base. Quantity: approximately 5 on average on a stem length of 10 cm. Length: approximately 6 mm on average. Color: near Yellow-Green Group 144D. On adult stems: Configuration: curved downwards on the upper surface and slightly concave on the under surface with an oval base. Quantity: approximately 9 on average on a stem length of 10 cm. Length: approximately 1.2 cm on average. Color: near Greyed-Orange Group 173A.

Leaves:

*Stipules*.—Adnate, pectinate, rather broad, approximately 2 cm in length on average, approximately 5 mm in width on average, near Yellow-Green Group 147D on the upper surface, and near Yellow-Green Group 147C on the under surface.

*Petioles*.—Upper surface: near Yellow-Green Group 145A in coloration. Under surface: near Green Group 138C in coloration. Texture: non-glandular on the upper surface, and with a few small prickles on the under surface.

*Rachis*.—Upper surface: near Yellow-Green Group 147D in coloration. Under surface: near Yellow-Green Group 147C in coloration. General appearance: rather dense.

*Leaflets*.—Number: 3, 5 and 7 (most often). Shape: generally elliptical with a cuneiform tip and an obtuse base. Size: the terminal leaflets commonly are approximately 3.5 cm in length on average and approximately 2.1 cm in width on average. Serration: slightly denticulate, small and single (as illustrated). Texture: physically firm and leathery with a glossy upper surface. Color (young foliage): Upper surface: near Green Group 137B. Under surface: near Green Group 138B. Color (adult foliage): Upper surface: near Green Group 137C. Under surface: near Yellow-Green Group 138B.

Inflorescence:

*Number of flowers*.—Commonly approximately 8 to 20 blossoms per stem.

*Peduncle*.—Pubescent, approximately 2.8 cm in length on average, approximately 2 mm in diameter on average, and near Yellow-Green Group 144A in coloration.

*Sepals*.—Upper surface: tomentose and near Yellow-Green Group 147C in coloration. Under surface: smooth and near Yellow-Green Group 144A in coloration. Shape: longish and narrow, and somewhat rounded at the base. Size: approximately 1.4 cm in length on average, and approximately 7 mm in width at the widest point on average.

*Buds*.—Shape: substantially conical. Size: small. Length: approximately 1.2 cm on average. Width: approximately 9 mm at the widest point on average. Color as calyx breaks: Upper surface: near Red Group 45A. Under surface: near Red-Purple Group 61B.

*Flower*.—Shape: cup-shaped. Diameter approximately 3 to 4 cm on average. Color (in the course of opening): Upper surface: near Red Group 46B with a spot of near White Group 155A at the base. Under surface: near Red-Purple Group 63A with a spot of near White Group 63A at the base. Color (open flower): Upper side: near Red Group 53C suffused with near Red Group 46B with a spot of near White Group 155A at the base. Under side: near Red-Purple Group 63A with a spot of White Group 155A at the base. Fragrance: none detected. Petal number: approximately 18 on average under normal growing conditions. Petal shape: with a substantially rounded tip and an obtuse base. Petal texture: leathery and somewhat firm. Petal length: approximately 2.3 cm on average. Petal width: approximately 2 cm on average. Petal arrangement: imbricated, and without petaloids. Petal drop: good with the petals commonly detaching cleanly before drying. Stamen number: approximately 134 on average. Anthers: regularly arranged around the styles, approximately 2 mm in size on average, and near Greyed-Orange Group 167C in coloration. Filaments: approximately 4 mm in length on average, and near Yellow-Green Group 149C in coloration. Pollen: none available for observation. Pistils: approximately 34 on average. Stigmas: approximately 1 mm in size on average, and near Yellow-Green Group 150C in coloration. Styles: approximately 4 mm in length on average, and near Yellow-Green Group 151D in coloration. Fruit: commonly small and rounded in configuration and formed in a sparse quantity when observed. Receptacle: smooth, pitcher-shaped in longitudinal section, approximately 7 mm in length on average, approximately 6 mm in width on average at the widest point, and near Yellow-Green Group 144A in coloration.

Development:

*Vegetation*.—Strong.

*Blooming*.—Early season, very abundant and substantially continuous.

*Tolerance to diseases*.—Good, with no particular susceptibility to common diseases having been encountered during observations to date.

The new 'Meigremlis' variety has not been observed under all possible environmental conditions to date. Accordingly, it is possible that the phenotypic expression may vary somewhat with changes in light intensity and duration, cultural practices, and other environmental conditions.

I claim:

1. A new and distinct Floribunda rose plant characterized by the following characteristics:

(a) displays a low and compact bushy growth habit with strong vegetation with the plant commonly displaying a well-ordered overall appearance until late in the season, (b) forms in abundance on a substantially continuous basis attractive red semi-double blossoms, (c) exhibits rather dense dark green foliage with a glossy aspect on the upper surface, and (d) is particularly well suited for providing attractive ornamentation in parks and gardens;

substantially as shown and described.

* * * * *

MEIGREMLIS